(12) United States Patent
Kawamura et al.

(10) Patent No.: US 6,762,296 B2
(45) Date of Patent: Jul. 13, 2004

(54) ANTITUMOR PROTEIN AND CORRESPONDING GENE SEQUENCE ISOLATED FROM MATSUTAKE MUSHROOMS

(75) Inventors: Yukio Kawamura, Tsukuba (JP); Akihiro Morita, Kasukabe (JP); Koji Izumo, Kasukabe (JP); Tomohide Saka, Tsukuba (JP)

(73) Assignee: Independent Administrative Food Research institute (JP)

( * ) Notice: Subject to any disclaimer, the term of this patent is extended or adjusted under 35 U.S.C. 154(b) by 0 days.

(21) Appl. No.: 09/911,969

(22) Filed: Jul. 24, 2001

(65) Prior Publication Data

US 2002/0137896 A1 Sep. 26, 2002

Related U.S. Application Data

(62) Division of application No. 09/023,731, filed on Feb. 13, 1998, now Pat. No. 6,291,648.

(30) Foreign Application Priority Data

Feb. 13, 1997 (JP) .............................................. 9-029275

(51) Int. Cl.$^7$ .............................................. C07H 21/04
(52) U.S. Cl. ................................ 536/23.74; 435/320.1; 530/350
(58) Field of Search .............................. 536/23.1, 23.74, 536/24.1; 435/320.1, 69.1, 325, 252.1, 252.33, 255.1; 530/350, 300

(56) References Cited

U.S. PATENT DOCUMENTS

| | | | |
|---|---|---|---|
| 5,302,699 A | | 4/1994 | Kawamura et al. |
| 5,874,546 A | * | 2/1999 | Nagata et al. |
| 6,300,474 B1 | * | 10/2001 | Pestka |

OTHER PUBLICATIONS

Cameron, 1997, Molec. Biol. 7, pp. 253–265.*
Mullins (1993, Hypertension, vol. 22, pp. 630–633.*
Mullins (1990, Nature, vol. 344, 541–544.*
Hammer (1990, Cell, vol. 63, 1099–1112.*
Mullins, 1989, EMBO J., vol. 8, pp. 4065–4072.*
Taurog, 1988, Jour. Immunol., vol. 141, pp. 4020–4023).*
Mullins (1996, J. Clin. Invest. vol. 98, pp. S37–S40).*
Stratagene online catalog for YRG–2 yeast, 2003.*
ATCC online catalog for FR3T3 and 3T3 cell, 2003.*
USCD core cell culture Facility online catalog for HB101 cell, 2003.*
Overbeek (1994, "Factors affecting transgenic animal production," Transgenic animal technology, pp. 96–98.*
Wall, 1996 Theriogenology, vol. 45, pp. 57–68.*
Houdebine, 1994, J. Biotech. vol. 34, pp. 269–287.*
Kappell, 1992, Current Opinions in Biotechnology, vol. 3, pp. 548–553.*
Hurtenbach, et al., J. Exp. Med. 177:1499–1504 1993.
Mathews, et al, Biochemistry, The Benjamin/Cummings Publishing Company, Inc., pp 213–215 1990.
Gura Science 278:1041–42 1997.
Burgess, et al., J. Of Cell Biology 111:2129–38 1990.
Lin, et al., Biochemistry 14:1559–63 1975.
Schwartz, et al., Proc. Natl. Acad. Sci. USA 84:6408–6411 1987.
Lazar, et al., Mol. Cell. Biol. 8:1247–52 1993.

* cited by examiner

*Primary Examiner*—Larry R. Helms
(74) *Attorney, Agent, or Firm*—Morgan & Finnegan, LLP

(57) ABSTRACT

An objective of the present invention is to provide an antitumor protein and a gene encoding the same. The specification discloses a protein comprising (a) an amino acid sequence of SEQ ID No.1 or (b) a modified amino acid sequence of SEQ ID No.1 which have antitumor activity wherein one or more amino acids are added and/or inserted into the amino acid sequence of SEQ ID No.1 and/or one or more amino acids in the amino acid sequence of SEQ ID No.1 are substituted and/or deleted.

13 Claims, 2 Drawing Sheets

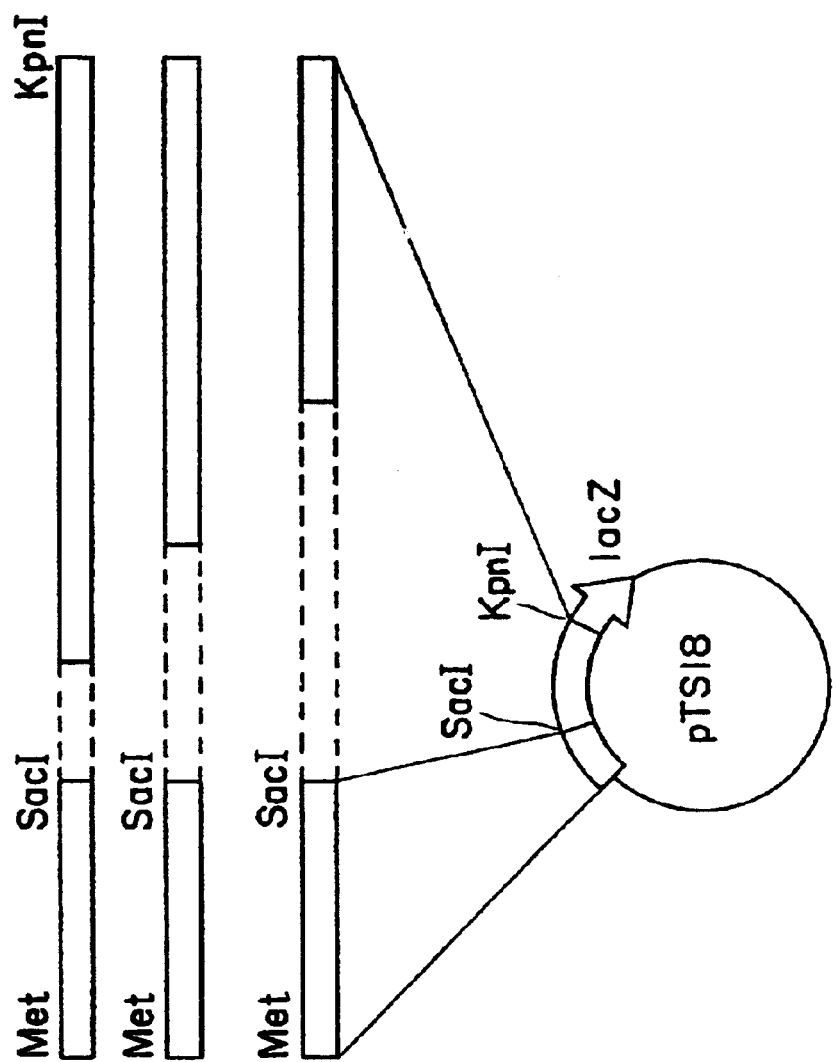
F I G. 2

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH: 566
      (B) TYPE: amino acid
      (D) TOPOLOGY: linear (ii) MOLECULE TYPE: protein (xi) SEQUENCE DESCRIPTION: SEQ ID NO: 1:

```
Met Pro Ile Arg Leu Ser Lys Glu Lys Ile Asn Asp Leu Leu Gln Arg
 1               5                  10                  15

Ser Gln Gly Asp Leu Thr Ser Ser Gln His Glu Ile Val His Phe Thr
                20                  25                  30

Asp Val Phe Ile Ala Gly Ser Gly Pro Ile Ser Cys Thr Tyr Ala Arg
            35                  40                  45

His Ile Ile Asp Asn Thr Ser Thr Thr Lys Val Tyr Met Ala Glu Ile
        50                  55                  60

Gly Ser Gln Asp Asn Pro Val Ile Gly Ala His Lys Asn Ser Ile
 65                 70                  75                  80

Lys Phe Gln Lys Asp Ile Asp Lys Phe Val Asn Ile Ile Asn Gly Ala
                85                  90                  95

Leu Gln Pro Ile Ser Ile Ser Pro Ser Asp Thr Tyr Gln Pro Thr Leu
                100                 105                 110

Ala Val Ala Ala Trp Ala Pro Pro Ile Asp Pro Ala Glu Gly Gln Leu
            115                 120                 125

Val Ile Met Gly His Asn Pro Asn Gln Glu Ala Gly Leu Asn Leu Pro
        130                 135                 140

Gly Ser Ala Val Thr Arg Thr Val Gly Gly Met Ala Thr His Trp Thr
145                 150                 155                 160

Cys Ala Cys Pro Thr Pro His Asp Glu Glu Arg Val Asn Asn Pro Val
                165                 170                 175

Asp Lys Gln Glu Phe Asp Ala Leu Leu Glu Arg Ala Lys Thr Leu Leu
                180                 185                 190

Asn Val His Ser Asp Gln Tyr Asp Asp Ser Ile Arg Gln Ile Val Val
                195                 200                 205

Lys Glu Thr Leu Gln Gln Thr Leu Asp Ala Ser Arg Gly Val Thr Thr
210                 215                 220

Leu Pro Leu Gly Val Glu Arg Arg Thr Asp Asn Pro Ile Tyr Val Thr
225                 230                 235                 240

Trp Thr Gly Ala Asp Thr Val Leu Gly Asp Val Pro Lys Ser Pro Arg
                245                 250                 255

Phe Ala Leu Val Thr Glu Thr Arg Val Thr Lys Leu Ile Val Ser Glu
                260                 265                 270

Thr Asn Pro Thr Gln Val Val Ala Ala Leu Leu Arg Asn Leu Asn Thr
                275                 280                 285

Ser Asn Asp Glu Leu Val Val Ala Lys Ser Phe Val Ile Ala Cys Gly
                290                 295                 300

Ala Val Cys Thr Pro Gln Ile Leu Trp Asn Ser Asn Ile Arg Pro Tyr
305                 310                 315                 320
```

-continued

```
Ala Leu Gly Arg Tyr Leu Ser Glu Gln Ser Met Thr Phe Cys Gln Ile
            325                 330                 335

Val Leu Lys Arg Gly Ile Val Asp Ala Ile Ala Thr Asp Pro Arg Phe
            340                 345                 350

Ala Ala Lys Val Glu Ala His Lys Lys His Pro Asp Asp Val Leu
            355                 360                 365

Pro Ile Pro Phe His Glu Pro Glu Pro Gln Val Met Ile Pro Tyr Thr
370                 375                 380

Ser Asp Phe Pro Trp His Val Gln Val His Arg Asp Ala Phe Ser Tyr
385                 390                 395                 400

Gly Asp Val Gly Pro Lys Ala Asp Pro Arg Val Val Asp Leu Arg
                405                 410                 415

Phe Phe Gly Lys Ser Asp Ile Val Glu Glu Asn Arg Val Thr Phe Gly
            420                 425                 430

Pro Asn Pro Lys Leu Arg Glu Trp Glu Ala Gly Val Thr Asp Thr Tyr
            435                 440                 445

Gly Met Pro Gln Pro Thr Phe His Val Lys Arg Thr Asn Ala Asp Gly
            450                 455                 460

Asp Arg Asp Gln Arg Met Met Asn Asp Met Thr Asn Val Ala Asn Met
465                 470                 475                 480

Leu Gly Gly Tyr Leu Pro Gly Ser Tyr Pro Gln Phe Met Ala Pro Gly
            485                 490                 495

Leu Val Leu His Ile Thr Gly Thr Thr Arg Ile Gly Thr Asp Asp Gln
                500                 505                 510

Thr Ser Val Ala Asp Pro Thr Ser Lys Val His Asn Phe Asn Asn Leu
            515                 520                 525

Trp Val Gly Gly Asn Gly Cys Ile Pro Asp Ala Thr Ala Cys Asn Pro
            530                 535                 540

Thr Arg Thr Ser Val Ala Tyr Ala Leu Lys Gly Ala Glu Ala Val Val
545                 550                 555                 560

Asn Tyr Leu Gly Val Ser
            565

(2) INFORMATION FOR SEQ ID NO: 2:

(i) SEQUENCE CHARACTERISTICS:
        (A) LENGTH: 1701
        (B) TYPE: nucleic acid
        (C) TOPOLOGY: linear
        (D) STRANDNESS: Single (ii) MOLECULE TYPE: cDNA to RNA (xi) SEQUENCE DESCRIPTION: SEQ ID NO: 2:

ATG CCG ATA CGT CTT TCC AAA GAA AAA ATC AAC GAC CTG CTG CAA CGT     48
Met Pro Ile Arg Leu Ser Lys Glu Lys Ile Asn Asp Leu Leu Gln Arg
1               5                   10                  15

TCT CAA GGG GAT CTT ACT TCC TCG CAA CAC GAA ATT GTA CAT TTC ACT     96
Ser Gln Gly Asp Leu Thr Ser Ser Gln His Glu Ile Val His Phe Thr
                20                  25                  30

GAT GTT TTC ATT GCT GGC AGT GGT CCC ATT AGC TGT ACT TAC GCC CGC    144
Asp Val Phe Ile Ala Gly Ser Gly Pro Ile Ser Cys Thr Tyr Ala Arg
            35                  40                  45

CAC ATC ATT GAC AAT ACC TCA ACT ACA AAG GTT TAC ATG GCC GAA ATA    192
His Ile Ile Asp Asn Thr Ser Thr Thr Lys Val Tyr Met Ala Glu Ile
        50                  55                  60

GGT TCT CAA GAT AAC CCT GTC ATC GGG GCC CAT CAC AAG AAC TCC ATA    240
Gly Ser Gln Asp Asn Pro Val Ile Gly Ala His His Lys Asn Ser Ile
```

```
                     65                    70                    75                    80
AAG TTT CAG AAA GAC ATT GAC AAG TTT GTG AAT ATC ATC AAC GGT GCC                        288
Lys Phe Gln Lys Asp Ile Asp Lys Phe Val Asn Ile Ile Asn Gly Ala
                    85                    90                    95

CTC CAG CCG ATT TCG ATT TCG CCA TCG GAC ACC TAC CAG CCC ACT CTC                        336
Leu Gln Pro Ile Ser Ile Ser Pro Ser Asp Thr Tyr Gln Pro Thr Leu
                100                   105                   110

GCT GTA GCA GCG TGG GCG CCG CCC ATC GAT CCT GCC GAA GGC CAG CTC                        384
Ala Val Ala Ala Trp Ala Pro Pro Ile Asp Pro Ala Glu Gly Gln Leu
            115                   120                   125

GTG ATT ATG GGA CAC AAT CCG AAT CAG GAG GCC GGC CTG AAC CTT CCC                        432
Val Ile Met Gly His Asn Pro Asn Gln Glu Ala Gly Leu Asn Leu Pro
        130                   135                   140

GGT AGC GCT GTC ACT AGG ACA GTC GGG GGG ATG GCG ACC CAC TGG ACT                        480
Gly Ser Ala Val Thr Arg Thr Val Gly Gly Met Ala Thr His Trp Thr
145                   150                   155                   160

TGC GCG TGT CCT ACT CCA CAT GAC GAA GAG AGG GTC AAC AAC CCA GTT                        528
Cys Ala Cys Pro Thr Pro His Asp Glu Glu Arg Val Asn Asn Pro Val
                165                   170                   175

GAC AAG CAG GAG TTC GAC GCA CTG CTC GAA CGT GCT AAA ACA TTG CTC                        576
Asp Lys Gln Glu Phe Asp Ala Leu Leu Glu Arg Ala Lys Thr Leu Leu
            180                   185                   190

AAC GTT CAC AGC GAC CAG TAC GAC GAT TCT ATC CGT CAG ATA GTT GTC                        624
Asn Val His Ser Asp Gln Tyr Asp Asp Ser Ile Arg Gln Ile Val Val
        195                   200                   205

AAA GAG ACT CTT CAG CAG ACC CTT GAT GCG TCG CGG GGT GTG ACC ACT                        672
Lys Glu Thr Leu Gln Gln Thr Leu Asp Ala Ser Arg Gly Val Thr Thr
    210                   215                   220

CTC CCG CTG GGG GTG GAG CGC CGT ACG GAC AAT CCT ATT TAT GTC ACC                        720
Leu Pro Leu Gly Val Glu Arg Arg Thr Asp Asn Pro Ile Tyr Val Thr
225                   230                   235                   240

TGG ACC GGT GCC GAT ACC GTC CTT GGT GAT GTG CCG AAG AGT CCC CGA                        768
Trp Thr Gly Ala Asp Thr Val Leu Gly Asp Val Pro Lys Ser Pro Arg
                245                   250                   255

TTC GCT TTG GTT ACA GAG ACG AGA GTG ACG AAG CTT ATT GTC AGT GAA                        816
Phe Ala Leu Val Thr Glu Thr Arg Val Thr Lys Leu Ile Val Ser Glu
            260                   265                   270

ACC AAT CCG ACG CAG GTT GTT GCT GCG TTG CTA CGT AAC TTG AAT ACA                        864
Thr Asn Pro Thr Gln Val Val Ala Ala Leu Leu Arg Asn Leu Asn Thr
        275                   280                   285

AGC AAC GAT GAA CTT GTC GTG GCC AAG AGT TTC GTC ATA GCT TGT GGA                        912
Ser Asn Asp Glu Leu Val Val Ala Lys Ser Phe Val Ile Ala Cys Gly
    290                   295                   300

GCA GTC TGC ACA CCG CAA ATC TTG TGG AAC AGC AAC ATC CGC CCA TAT                        960
Ala Val Cys Thr Pro Gln Ile Leu Trp Asn Ser Asn Ile Arg Pro Tyr
305                   310                   315                   320

GCG CTT GGT CGC TAC CTC AGC GAA CAG TCC ATG ACT TTT TGT CAG ATC                       1008
Ala Leu Gly Arg Tyr Leu Ser Glu Gln Ser Met Thr Phe Cys Gln Ile
                325                   330                   335

GTT CTC AAG AGG GGC ATA GTC GAT GCC ATC GCT ACT GAC CCT CGC TTC                       1056
Val Leu Lys Arg Gly Ile Val Asp Ala Ile Ala Thr Asp Pro Arg Phe
            340                   345                   350

GCT GCG AAG GTT GAG GCG CAC AAG AAG AAG CAC CCC GAT GAC GTG CTG                       1104
Ala Ala Lys Val Glu Ala His Lys Lys Lys His Pro Asp Asp Val Leu
        355                   360                   365

CCC ATT CCA TTC CAC GAG CCT GAA CCT CAA GTG ATG ATT CCG TAC ACG                       1152
Pro Ile Pro Phe His Glu Pro Glu Pro Gln Val Met Ile Pro Tyr Thr
    370                   375                   380

TCG GAC TTC CCT TGG CAT GTT CAG GTG CAT CGC GAT GCA TTC TCA TAT                       1200
```

```
Ser Asp Phe Pro Trp His Val Gln Val His Arg Asp Ala Phe Ser Tyr
385                 390                 395                 400

GGT GAT GTT GGA CCC AAG GCC GAC CCG CGT GTT GTC GTC GAT CTG AGG    1248
Gly Asp Val Gly Pro Lys Ala Asp Pro Arg Val Val Val Asp Leu Arg
                405                 410                 415

TTT TTC GGC AAA TCA GAT ATT GTC GAA GAA AAT CGA GTG ACT TTC GGT    1296
Phe Phe Gly Lys Ser Asp Ile Val Glu Glu Asn Arg Val Thr Phe Gly
                420                 425                 430

CCG AAC CCT AAG CTA CGC GAG TGG GAA GCG GGT GTT ACA GAC ACT TAT    1344
Pro Asn Pro Lys Leu Arg Glu Trp Glu Ala Gly Val Thr Asp Thr Tyr
                435                 440                 445

GGA ATG CCA CAG CCG ACA TTC CAT GTC AAG CGG ACC AAC GCC GAT GGA    1392
Gly Met Pro Gln Pro Thr Phe His Val Lys Arg Thr Asn Ala Asp Gly
                450                 455                 460

GAC CGT GAC CAG AGG ATG ATG AAT GAT ATG ACC AAC GTC GCG AAC ATG    1440
Asp Arg Asp Gln Arg Met Met Asn Asp Met Thr Asn Val Ala Asn Met
465                 470                 475                 480

CTG GGT GGG TAC CTT CCT GGC TCC TAC CCT CAA TTT ATG GCA CCT GGT    1488
Leu Gly Gly Tyr Leu Pro Gly Ser Tyr Pro Gln Phe Met Ala Pro Gly
                485                 490                 495

CTC GTA CTG CAC ATC ACG GGA ACT ACT CGG ATC GGG ACA GAT GAT CAA    1536
Leu Val Leu His Ile Thr Gly Thr Thr Arg Ile Gly Thr Asp Asp Gln
                500                 505                 510

ACT TCT GTT GCT GAT CCG ACA TCA AAG GTT CAT AAC TTC AAC AAT CTG    1584
Thr Ser Val Ala Asp Pro Thr Ser Lys Val His Asn Phe Asn Asn Leu
                515                 520                 525

TGG GTC GGC GGG AAT GGG TGC ATT CCA GAT GCG ACT GCC TGC AAC CCG    1632
Trp Val Gly Gly Asn Gly Cys Ile Pro Asp Ala Thr Ala Cys Asn Pro
                530                 535                 540

ACT CGT ACG AGC GTC GCG TAT GCG CTC AAG GGT GCT GAG GCT GTA GTC    1680
Thr Arg Thr Ser Val Ala Tyr Ala Leu Lys Gly Ala Glu Ala Val Val
545                 550                 555                 560

AAT TAC CTT GGC GTC TCC TGA                                        1701
Asn Tyr Leu Gly Val Ser  *
                565

(2) INFORMATION FOR SEQ ID NO: 3:

(i) SEQUENCE CHARACTERISTICS:
        (A) LENGTH: 29
        (B) TYPE: amino acid
        (D) TOPOLOGY: linear (ii) MOLECULE TYPE: peptide (xi) SEQUENCE DESCRIPTION: SEQ ID NO: 3:

Pro Ile Arg Leu Ser Lys Glu Lys Ile Asn Asp Leu Leu Gln Arg Ser
1               5                   10                  15

Gln Gly Asp Leu Thr Ser Ser Gln His Glu Ile Val His
            20                  25

(2) INFORMATION FOR SEQ ID NO: 4:

(i) SEQUENCE CHARACTERISTICS:
        (A) LENGTH: 57
        (B) TYPE: amino acid
        (D) TOPOLOGY: linear (ii) MOLECULE TYPE: peptide (xi) SEQUENCE DESCRIPTION: SEQ ID NO: 4:

Pro Ile Arg Leu Ser Lys Glu Lys Ile Asn Asp Leu Leu Gln Arg Ser
1               5                   10                  15
```

```
Gln Gly Asp Leu Thr Ser Ser Gln His Glu Ile Val His Phe Thr Asp
            20                  25                  30

Val Phe Ile Ala Gly Ser Gly Pro Ile Ser Cys Thr Tyr Ala Arg His
            35                  40                  45

Ile Ile Asp Asn Thr Ser Thr Thr Lys
    50                  55
```

(2) INFORMATION FOR SEQ ID NO: 5:

(i) SEQUENCE CHARACTERISTICS:
        (A) LENGTH: 19
        (B) TYPE: amino acid
        (D) TOPOLOGY: linear (ii) MOLECULE TYPE: peptide (xi) SEQUENCE DESCRIPTION: SEQ ID NO: 5:

```
Val Tyr Met Ala Glu Ile Gly Ser Gln Asp Asn Pro Val Ile Gly Ala
1               5                   10                  15

His His Lys
```

(2) INFORMATION FOR SEQ ID NO: 6:

(i) SEQUENCE CHARACTERISTICS:
        (A) LENGTH: 61
        (B) TYPE: amino acid
        (D) TOPOLOGY: linear (ii) MOLECULE TYPE: peptide (xi) SEQUENCE DESCRIPTION: SEQ ID NO: 6:

```
Phe Val Asn Ile Ile Asn Gly Ala Leu Gln Pro Ile Ser Ile Ser Pro
1               5                   10                  15

Ser Asp Thr Tyr Gln Pro Thr Leu Ala Val Ala Ala Trp Ala Pro Pro
            20                  25                  30

Ile Asp Pro Ala Glu Gly Gln Leu Val Ile Met Gly His Asn Pro Asn
            35                  40                  45

Gln Glu Ala Gly Leu Asn Leu Pro Gly Ser Ala Val Thr
    50                  55                  60
```

(2) INFORMATION FOR SEQ ID NO: 7:

(i) SEQUENCE CHARACTERISTICS:
        (A) LENGTH: 29
        (B) TYPE: amino acid
        (D) TOPOLOGY: linear (ii) MOLECULE TYPE: peptide (xi) SEQUENCE DESCRIPTION: SEQ ID NO: 7:

```
Arg Thr Val Gly Gly Met Ala Thr His Trp Thr Cys Ala Cys Pro Thr
1               5                   10                  15

Pro His Asp Glu Glu Arg Val Asn Asn Pro Val Asp Lys
            20                  25
```

(2) INFORMATION FOR SEQ ID NO: 8:

(i) SEQUENCE CHARACTERISTICS:
        (A) LENGTH: 31
        (B) TYPE: amino acid
        (D) TOPOLOGY: linear (ii) MOLECULE TYPE: peptide (xi) SEQUENCE DESCRIPTION: SEQ ID NO: 8:

Gln Glu Phe Asp Ala Leu Leu Glu Arg Ala Lys Thr Leu Leu Asn Val
1               5                   10                  15

His Ser Asp Gln Tyr Asp Asp Ser Ile Arg Gln Ile Val Val Lys
            20                  25                  30

(2) INFORMATION FOR SEQ ID NO: 9:

(i) SEQUENCE CHARACTERISTICS:
        (A) LENGTH: 58
        (B) TYPE: amino acid
        (D) TOPOLOGY: linear (ii) MOLECULE TYPE: peptide (xi) SEQUENCE DESCRIPTION: SEQ ID NO: 9:

Glu Thr Leu Gln Gln Thr Leu Asp Ala Ser Arg Gly Val Thr Thr Leu
1               5                   10                  15

Pro Leu Gly Val Glu Arg Arg Thr Asp Asn Pro Ile Tyr Val Thr Trp
            20                  25                  30

Thr Gly Ala Asp Thr Val Leu Gly Asp Val Pro Lys Ser Pro Arg Phe
        35                  40                  45

Ala Leu Val Thr Glu Thr Arg Val Thr Lys
    50                  55

(2) INFORMATION FOR SEQ ID NO: 10:

(i) SEQUENCE CHARACTERISTICS:
        (A) LENGTH: 30
        (B) TYPE: amino acid
        (D) TOPOLOGY: linear (ii) MOLECULE TYPE: peptide (xi) SEQUENCE DESCRIPTION: SEQ ID NO: 10:

Leu Ile Val Ser Glu Thr Asn Pro Thr Gln Val Val Ala Ala Leu Leu
1               5                   10                  15

Arg Asn Leu Asn Thr Ser Asn Asp Glu Leu Val Val Ala Lys
            20                  25                  30

(2) INFORMATION FOR SEQ ID NO: 11:

(i) SEQUENCE CHARACTERISTICS:
        (A) LENGTH: 58
        (B) TYPE: amino acid
        (D) TOPOLOGY: linear (ii) MOLECULE TYPE: peptide (xi) SEQUENCE DESCRIPTION: SEQ ID NO: 11:

Ser Phe Val Ile Ala Cys Gly Ala Val Cys Thr Pro Gln Ile Leu Trp
1               5                   10                  15

Asn Ser Asn Ile Arg Pro Tyr Ala Leu Gly Arg Tyr Leu Ser Glu Gln
            20                  25                  30

Ser Met Thr Phe Cys Gln Ile Val Leu Lys Arg Gly Ile Val Asp Ala
        35                  40                  45

Ile Ala Thr Asp Pro Arg Phe Ala Ala Lys
    50                  55

(2) INFORMATION FOR SEQ ID NO: 12:

(i) SEQUENCE CHARACTERISTICS:
        (A) LENGTH: 51

```
        (B) TYPE: amino acid
        (D) TOPOLOGY: linear (ii) MOLECULE TYPE: peptide (xi) SEQUENCE DESCRIPTION: SEQ ID NO: 12:

Val Glu Ala His Lys Lys Lys His Pro Asp Asp Val Leu Pro Ile Pro
1               5                   10                  15

Phe His Glu Pro Glu Pro Gln Val Met Ile Pro Tyr Thr Ser Asp Phe
            20                  25                  30

Pro Trp His Val Gln Val His Arg Asp Ala Phe Ser Tyr Gly Asp Val
        35                  40                  45

Gly Pro Lys
        50

(2) INFORMATION FOR SEQ ID NO: 13:

(i) SEQUENCE CHARACTERISTICS:
        (A) LENGTH: 30
        (B) TYPE: amino acid
        (D) TOPOLOGY: linear (ii) MOLECULE TYPE: peptide (xi) SEQUENCE DESCRIPTION: SEQ ID NO: 13:

Ala Asp Pro Arg Val Val Asp Leu Arg Phe Phe Gly Lys Ser Asp
1               5                   10                  15

Ile Val Glu Glu Asn Arg Val Thr Phe Gly Pro Asn Pro Lys
            20                  25                  30

(2) INFORMATION FOR SEQ ID NO: 14:

(i) SEQUENCE CHARACTERISTICS:
        (A) LENGTH: 50
        (B) TYPE: amino acid
        (D) TOPOLOGY: linear (ii) MOLECULE TYPE: peptide (xi) SEQUENCE DESCRIPTION: SEQ ID NO: 14:

Leu Arg Glu Trp Glu Ala Gly Val Thr Asp Thr Tyr Gly Met Pro Gln
1               5                   10                  15

Pro Thr Phe His Val Lys Arg Thr Asn Ala Asp Gly Asp Arg Asp Gln
            20                  25                  30

Arg Met Met Asn Asp Met Thr Asn Val Ala Asn Met Leu Gly Gly Tyr
        35                  40                  45

Leu Pro
    50

(2) INFORMATION FOR SEQ ID NO: 15:

(i) SEQUENCE CHARACTERISTICS:
        (A) LENGTH: 35
        (B) TYPE: amino acid
        (D) TOPOLOGY: linear (ii) MOLECULE TYPE: peptide (xi) SEQUENCE DESCRIPTION: SEQ ID NO: 15:

Gly Ser Tyr Pro Gln Phe Met Ala Pro Gly Leu Val Leu His Ile Thr
1               5                   10                  15

Gly Thr Thr Arg Ile Gly Thr Asp Asp Gln Thr Ser Val Ala Asp Pro
            20                  25                  30
```

```
Thr Ser Lys
        35
```

(2) INFORMATION FOR SEQ ID NO: 16:

(i) SEQUENCE CHARACTERISTICS:
        (A) LENGTH: 33
        (B) TYPE: amino acid
        (D) TOPOLOGY: linear (ii) MOLECULE TYPE: peptide (xi) SEQUENCE DESCRIPTION: SEQ ID NO: 16:

```
Val His Asn Phe Asn Asn Leu Trp Val Gly Gly Asn Gly Cys Ile Pro
1               5                   10                  15
Asp Ala Thr Ala Cys Asn Pro Thr Arg Thr Ser Val Ala Tyr Ala Leu
            20                  25                  30
Lys
```

(2) INFORMATION FOR SEQ ID NO: 17:

(i) SEQUENCE CHARACTERISTICS:
        (A) LENGTH: 12
        (B) TYPE: amino acid
        (D) TOPOLOGY: linear (ii) MOLECULE TYPE: peptide (xi) SEQUENCE DESCRIPTION: SEQ ID NO: 17:

```
Gly Ala Glu Ala Val Val Asn Tyr Leu Gly Val Ser
1               5                   10
```

(2) INFORMATION FOR SEQ ID NO: 18:

(i) SEQUENCE CHARACTERISTICS:
        (A) LENGTH: 22
        (B) TYPE: amino acid
        (D) TOPOLOGY: linear (ii) MOLECULE TYPE: peptide (xi) SEQUENCE DESCRIPTION: SEQ ID NO: 18:

```
Asn Ser Ile Lys Phe Gln Lys Asp Ile Asp Lys Phe Val Asn Ile Ile
1               5                   10                  15
Asn Gly Ala Leu Gln Pro
            20
```

(2) INFORMATION FOR SEQ ID NO: 19:

(i) SEQUENCE CHARACTERISTICS:
        (A) LENGTH: 26
        (B) TYPE: nucleic acid
        (C) STRANDEDNESS: Single
        (D) TOPOLOGY: linear (ii) MOLECULE TYPE: synthetic DNA (xi) SEQUENCE DESCRIPTION: SEQ ID NO: 19:

```
GAGAGACCAT GGGGTATCGT CTTTCC                                    26
```

(2) INFORMATION FOR SEQ ID NO: 20:

(i) SEQUENCE CHARACTERISTICS:
        (A) LENGTH: 27
        (B) TYPE: nucleic acid
        (C) STRANDEDNESS: Single
        (D) TOPOLOGY: linear -continued (ii) MOLECULE TYPE: synthetic DNA (xi) SEQUENCE DESCRIPTION: SEQ ID NO: 20:

GAGAGAGGAT CCGGAGACGC CAAGGAT                                              27

US 6,762,296 B2

ANTITUMOR PROTEIN AND CORRESPONDING GENE SEQUENCE ISOLATED FROM MATSUTAKE MUSHROOMS

This application is a divisional of application Ser. No. 09/023,731, filed on Feb. 13, 1998, which is now U.S. Pat. No. 6,291,648, which claims the benefit of Japanese application No. 9-029275, filed Feb. 13, 1997.

BACKGROUND OF THE INVENTION

1. Field of the Invention

The present invention relates to an antitumor protein and an nucleotide sequence encoding the same.

2. Background Art

Various studies have been conducted on antitumor substances found in edible mushrooms.

For example, polysaccharides and glycoprotein from mushrooms which have antitumor activity are disclosed in Japanese Patent Laid-open Publication Nos.61214/1977, 74797/1980, 293923/1986, 70362/1993 and 80699/1994, Japanese Patent Publication Nos. 47518/1986, 47519/1986 and 26172/1991. It is also reported that mushrooms are found to have antitumor activity when administered.

However, there has been no report on an amino acid sequence of an antitumor protein derived from *Tricholoma matsutake* which directly kills a tumor cell and on a gene encoding said protein.

SUMMARY OF THE INVENTION

The inventors now have purified an antitumor protein derived from *Tricholoma matsutake* and determined an amino acid sequence as well as a cDNA sequence encoding the protein. Further, the inventors have successfully purified the cDNA sequence and obtained a recombinant antitumor protein expressed in *E. coli* which is transformed by introducing a vector comprising the cDNA sequence. The present invention is based on these findings.

Thus, an object of the present invention is to provide an antitumor protein, a fragment of said protein, a nucleotide molecule encoding said protein, a vector comprising said molecule, a host cell transformed by said vector, a process for preparing said protein, and an antibody against said protein.

The protein according to the present invention comprises (a) an amino acid sequence of SEQ ID No.1, or (b) a modified amino acid sequence of SEQ ID No.1 which has antitumor activity wherein one or more amino acids are added and/or inserted into the amino acid sequence of SEQ ID No.1 and/or one or more amino acids in the amino acid sequence of SEQ ID No.1 are substituted and/or deleted.

The protein according to the present invention is useful as an antitumor agent.

BRIEF DESCRIPTION OF THE DRAWINGS

FIG. 2 illustrates the deletion of the TTM gene. Dashed lines denote a deleted area.

DETAILED DESCRIPTION OF THE INVENTION

Protein

Figure 1:
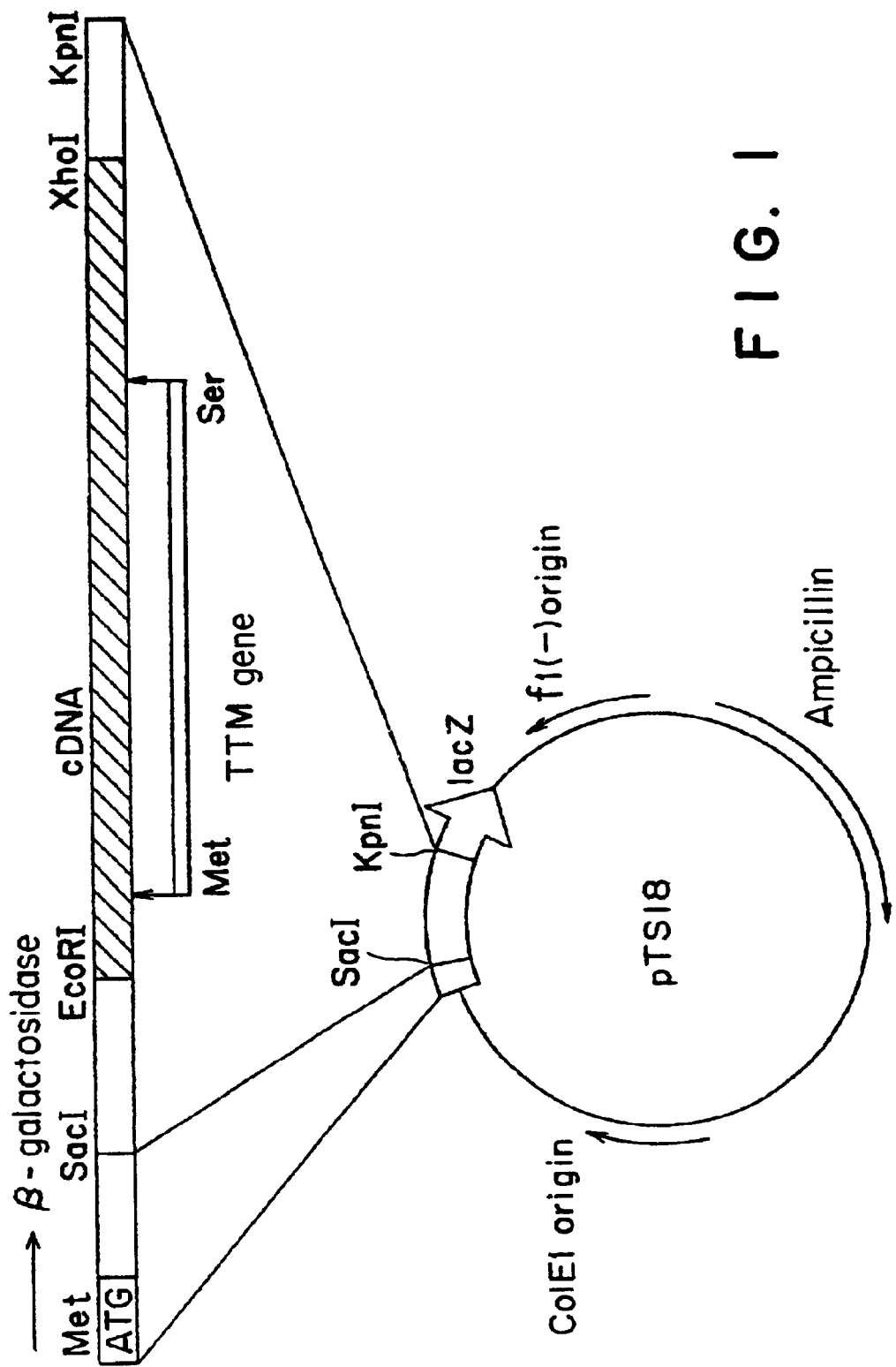
FIG. 1 illustrates the structure of plasmid vector pTS18.

The protein according to the present invention comprises the amino acid sequence of SEQ ID No.1. A protein consisting of the amino acid sequence of SEQ ID No.1 has antitumor activity as described in examples.

Examples of the proteins according to the present invention include those consisting of a modified amino acid sequence of SEQ ID No.1 which has antitumor activity wherein one or more amino acids are added and/or inserted into the amino acid sequence of SEQ ID NO.1 and/or one or more amino acids in the amino acid sequence of SEQ ID NO.1 are substituted and/or deleted. The terms "addition", "insertion", "substitution" and "deletion" refer to those which do not damage the antitumor activity of the protein consisting of the amino acid sequence of SEQ ID NO.1. The numbers of modifications such as additions, insertions, substitutions and deletions may be in the range between 1 and 8.

An addition, insertion, substitution or deletion may be introduced into an amino acid sequence in accordance with, for example, Molecular Cloning (A laboratory manual), second edition, Cold Spring Harbor Laboratory Press, Vol. 2, Chap. 15 (1989); Botstein, D. et al., Science, 229:1193 (1985); Craik, C. S., Bio. Techniques, 3:12 (1985); Itakura, K. et al., Annu. Rev. Biochem. 53:323 (1984); Shortle, D. et al., Annu. Rev. Genet. 15:265 (1981); or Smith, M. Annu. Rev. Genet. 19:423 (1985).

The wording "protein which have antitumor activity" as used herein refers to a protein which is evaluated by one skilled in the art to have antitumor activity, for example, a protein which is evaluated to have antitumor activity as tested under the conditions in Example 1 (3).

The molecular weight of the protein consisting of the amino acid sequence of SEQ ID NO.1 is about 65 kDa as measured by SDS-PAGE.

The amino acid sequence of SEQ ID NO.1 can be prepared by expression of the DNA sequence of SEQ ID NO.2 in a bacteria using a common technique. The cDNA sequence can be prepared by screening a cDNA library derived from *Tricholoma matsutake* using an antibody against the antitumor protein as a probe (see Example 2).

The protein according to the present invention has antitumor activity. Therefore, the protein according to the present invention may be formulated in a pharmaceutical composition which is used in the treatment of tumor such as carcinoma of uterine cervix or corpus uteri, and a variety of cancers caused by abnormal expression of antioncogene p53 or pBR (e.g., carcinoma cutaneum, lung cancer, liver cancer, kidney cancer, and breast cancer).

The pharmaceutical composition according to the present invention may be administered to a mammal including a human perorally or parenterally (e.g., intramuscularly, intravenously, subcutaneously, intrarectally, percutaneously or pernasally) in a form suitable for peroral or parenteral administration. A formulation which directly reaches a target area (e.g., a tablet which dissolves at a specific site, a liniment, or an injection) may be preferably used in the treatment of tumor.

The protein according to the present invention may be formulated in oral drugs (e.g., tablets, capsules, granules, powder, pills, grains, troches) when considering stability of the protein and the drug delivery path; injectable drugs (e.g., for intravenous or intramuscular injection); intrarectal drugs; and soluble or insoluble suppositories depending on its intended use. The pharmaceutical composition in these forms may be prepared by conventional methods with pharmaceutically acceptable vehicles such as bulking agents and fillers; adjuvants such as binding agents, wetting agents, disintegrants, surfactants, lubricants, dispersers, buffering agents, and solution adjuvant; additives such as preservatives, antiseptics, flavouring agents, soothing agents, stabilizers, coloring agents, and sweeting agents. A dose for various treatments may be determined depending on the route of administration as well as the age, sex, and condition of the patient.

Nucleotide Sequence

The present invention provides a nucleotide sequence encoding the protein according to the present invention. Examples of such nucleotide sequences include those comprising all or part of the DNA sequence of SEQ ID NO.2. Other examples of such nucleotide sequences include those comprising all or part of the DNA sequence in SEQ ID NO.2.

As mentioned above, the DNA sequence of SEQ ID NO.2 was obtained from a cDNA library derived from *Tricholoma matsutake*. This DNA sequence contains an open reading frame of the protein which starts at ATG (1–3) and ends at TAA (1699–1701).

The amino acid sequence determines a number of possible base sequences that encode the amino acid sequence in SEQ ID NO.1.

When the amino acid sequence of the protein according to the present invention is given, a nucleotide sequence encoding the amino acid sequence is easily determined, and a variety of nucleotide sequences encoding the amino acid sequence of SEQ ID NO: 1 can be selected.

Thus, a nucleotide sequence encoding the protein according to the present invention include DNA sequences which degenarate as a result of the genetic code as to the DNA sequence of SEQ ID No.2 as well as RNA sequences corresponding to the DNA sequences.

The nucleotide sequence according to the present invention may be naturally occurred or obtained by synthesis. It may also be synthesized with a part of a sequence derived from the naturally occurring one. DNAs may typically be obtained by screening a chromosome library or a cDNA library in accordance with conventional methods in the field of genetic engineering, for example, by screening a chromosome library or a cDNA library with an appropriate DNA probe obtained based on information of the partial amino acid sequence. The nucleotide sequence according to the present invention can be prepared, for example, from *Tricholoma matsutake* cDNA library by using an oligonucleotide encoding a peptide selected from SEQ ID Nos.3–18 as a screening probe.

The nucleotide sequences from nature are not specifically restricted to any sources; but may be derived from *Tricholoma matsutake* or other sources.

Vectors and Transformed Cells

The present invention provides a vector comprising the nucleotide sequence according to the present invention in such a manner that the vector can be replicable and express the protein encoded by the nucleotide sequence in a host cell. In addition, according to the present invention, we provide a host cell transformed by the vector. There is no other restriction to the host-vector system. It may express proteins fused with other proteins. Examples of an expression system of a fusion protein include those expressing MBP (maltose binding protein), GST (glutathione-S-transferase), HA (hemagglutinin), polyhistidine, myc, and Fas.

Examples of such systems expressing fusion proteins include those expressing β-galactosidase, glutathione-S-transferase, and luciferase.

Examples of vectors include plasmid vectors (e.g., pBluescript SK(−), pBluescript SK(+), pGEX-4T, pGEX-5T, pRIT2T, pBPV, and pSVK3 (Pharmacia, etc.); ZAP Express, pYEUra3, pMAM, and pOG (Toyobo); pET-11a, b, c, and d, pET-20b, pET-28a, b, and c, and pET-32a and b (Novagen); pQE-10, 16, 30, 40, 50, 60, and 70) (Qiagen); virus vectors (e.g., retrovirus vectors and adenovirus vectors); and liposome vectors (e.g., cationic liposome vectors).

In order to prepare a desired protein in the host cell, the vector according to the present invention may have a sequence which regulate expression of the protein (e.g., a promoter sequence, a terminator sequence, or an enhancer sequence) or markers for selecting a host cell (e.g., a neomycin-resistant gene or a kanamycin-resistant gene). Further, the vector may have the nucleotide sequence according to the present invention in a repeted form (e.g., in a tandem form). Such additional sequences may be introduced into the vector. A host cell may be transformed by the vector by conventional methods.

The vector according to the present invention may be prepared by conventional methods and procedures of the genetic engineering field.

Examples of host cells include *E. coli* (e.g., SOLR, JM109, XL1-Blue MRF', SURE, TOP, and BL21(DE3)), yeast cells (e.g. YRG-2), *Bacillus subtilis*, animal cells (e.g., CHO cells, COS cells, human keratinocytes, COP-5, C127, mouse 3T3 cells, FR3T3, and HB101). The SOLR, SURE, and TOP strains are host cell names registered with the RIKEN Cell Bank, 3-1-1 Koyadai, Tsukuba, Ibaraki, 305-0074 JAPAN. The C127 cell line is deposited with the RIKEN Cell Bank, and has been assigned accession no. RCB0036.

The protein according to the present invention is obtained from the culture by culturing host cells which are transformed as described above in an appropriate medium. Therefore, the present invention provides a process for preparing the protein according to the present invention. Such a process enables mass production of an antitumor protein.

The culture of the transformed host cell and culture condition may essentially be the same as those for the cell to be used. In addition, the protein according to the present invention may be recovered from the culture medium and purified according to conventional methods, for example, chromatography such as ion exchange chromatography, gel filtration chromatography, and immunoaffinity chromatography Antibody The present invention provides an antibody against the protein according to the present invention. The term "antibody" as used herein includes a polyclonal antibody or a monoclonal antibody.

The antibody according to the present invention can be prepared by conventional methods, for example, by injecting the protein of SEQ ID NO.1 or a fragment thereof into an animal (e.g., rabbit, rat or mouse) together with suitable carriers (e.g., Freund's complete and incomplete adjuvants) and then purifying the serum from the animal after a certain period.

Specific reaction (i.e., immuno reaction) of the antibody may be used as an indicator of an antitumor protein. Therefore, the antibody according to the present invention may be used for purifying and screening an antitumor protein.

EXAMPLES

The present invention is further illustrated by the following Examples which are not intended as a limitation of the invention.

Example 1

Purification of Antitumor Protein (1) Purification of Protein

An antitumor protein was purified from commercially available (or wild) fresh *Tricholoma matsutake* by homogenizing it in accordance with conventional methods and then isolating using purifying procedures such as column chromatography, HPLC, and electrophoresis. The detailed procedure is as follows:

A Tris buffer solution containing NaCl and protease inhibitor (50 mM Tris-HCl (pH 7.5), 150 mM NaCl, 1 mM PMSF, 1 mM EDTA, 0.1 mM IAA (iodoacetamide), 1 μg/ml pepstatin A, and 1 μg/ml leupeptin) was used for the preliminary elution of the protein, followed by precipitation with ammonium sulfate (90% saturated ammonium sulfate). The precipitate was dialyzed with 25 mM Tris-HCl (pH 7.5) containing 1/10 the above protease inhibitor (PI) to desalt. Then, after DEAE Toyopearl (ion exchange chromatography), concentration of the active fraction, purification through phenyl Sepharose (hydrophobic chromatography), concentration of the active fraction, gel filtration by HPLC (TSK gel G3000SW), the purified protein was finally obtained.

In ion exchange chromatography and hydrophobic chromatography, 25 mM Tris-HCl (pH 7.5) containing PI was used as eluant. For linear concentration gradient, NaCl and $(NH_4)_2SO_4$ were used, respectively. In gel filtration, 0.1 M sodium phosphate buffer (pH 7.2) containing 0.1 M $Na_2SO_4$ and PI was used as eluant.

The sample obtained by gel filtration with HPLC was analyzed by SDS-PAGE. The protein on the gel, which was transferred to a PVDF membrane and stained with CBB, exhibited a single band (about 65 kDa).

It was found that when *Tricholoma matsutake* with no freshness was used or when no protease inhibitor was used in purifying procedures, yield and antitumor activity were found to be lower.

Some of the samples were recovered by staining the gel with CBB after SDS-PAGE, and cutting it to extract electrically. These samples were used to determine the amino acid sequence (Example 2).

It was also found that the protein can be purified by affinity chromatography using a column in which the antibody (see (2)) was bound to CNBr-activated Sepharose 6MB resin (Pharmacia).

(2) Polyclonal Antibody

A rabbit was immunized with the protein purified in (1) to prepare antiserum. The procedure is as follows:

The purified protein, 15 μg, was mixed with Freund's complete adjuvant, stirred intensely to emulsion, and subcutaneously injected to the back of a rabbit. After 3 weeks, the rabbit was boosted with 150 μg of the purified protein, which was mixed with Freund's incomplete adjuvant to give emulsion. Then, after 2 weeks, they were directly reboosted using 50 μg of antibody, and blood was collected from its earlobe 1 week later.

Next, 5 ml of antiserum was incubated at 56° C. for 30 min, mixed with 5 ml of PBS(-) and the same amount of saturated $(NH_4)_2SO_4$, and maintained still in iced water. After centrifugation, the precipitate was redissolved in sodium phosphate buffer solution and mixed with an additional amount of saturated $(NH_4)_2SO_4$ to a final $(NH_4)_2SO_4$ concentration of 20%. After centrifugation, the supernatant was recovered and mixed with an additional amount of saturated $(NH_4)_2SO_4$ to a final $(NH_4)_2SO_4$ concentration of 33%. After centrifugation, the precipitate was recovered and redissolved. It was then dialyzed and desalted, followed by ion exchange chromatography (DE52 resin), to give an IgG fraction.

(3) Antitumor Activity Test

Lethal activity was investigated on cells which had been transformed by simian virus 40 (SV40) and human papiloma virus (HPV) which were known to cause malignant alteration. More specifically, antitumor activity was estimated with lethal activity. When the protein purified in (1) above was given to the cells, the quantity of the tested protein necessary for 50% fatal activity of total cells was 10 ng/ml in SVT2 cells (transformed SV40 cells), 100 ng/ml in A31 cells (transformed SV40 cells), and 15–20 ng/ml in human preputial cells (transformed HPV16 cells).

Example 2 cDNA Cloning and Sequencing

The amino acid sequence at the N-terminal of the protein purified in Example 1 was determined (SEQ ID NOS.3 and 4) using a protein sequencer (Hewlett-Packard).

Also, the protein obtained in Example 1 was digested using lysyl endnuclease to give a number of peptide fragments. Among them, the amino acid sequences of 14 peptide fragments were determined (SEQ ID NOS.5–18).

On the other hand, *Tricholoma matsutake* mRNA was purified with oligo-dT Latex (oligo-dT particles; Takara), then with STRATAGENE ZAP-CDNA Synthesis Kit (available from Toyobo), to synthesize cDNA. After synthesized, the cDNA was packaged in vitro in lambda phage using Gigapak III Gold (Stratagene, available from Toyobo) to prepare a phage library.

Using the antibody obtained in Example 1 (2) as a probe, the phage library was screened for the antitumor gene. Twenty-one phages were tested positive. The procedure is as follows:

The concentration of the library was determined with titer. About 2,000 to 20,000 phages and 600 μl *E. coli* (XL1-Blue) were plated in 150 mm NZYM culture plates together with 6ml NZYM Top Agar (0.7%). They were incubated at 42° C. for 3–4 hours until plaques developed to suitable sizes of about 1 mm. Then, a 130–140 mm nitrocellulose membrane soaked with 10 mM IPTG was placed on each plate, and incubation was continued at 37° C. for 3 hours. After the plates were cooled at 4° C. for 1 hour or more, the nitrocellulose filters were removed from the plates, and shaken in TBS-T buffer solution containing 3% skim milk.

Next, the filters were soaked in the buffer solution of the primary antibody (Example 1 (2)), and gently shaken in TBS-T buffer solution containing 3% skim milk. The filters were then soaked in the buffer solution of secondary antibody conjugated to alkali phosphatase (AP), and washed with TBS-T buffer solution. After they were washed with alkali phosphatase (AP) buffer solution, positive phages were detected.

The resulting positive phages were transformed with SOLR strains (Stratagene) by in vivo excision, using ZAP-cDNA Synthesis Kit (available from Toyobo) according to a manufacturer's manual.

Plasmid pTS18 as shown in FIG. 1 was obtained from the transformants. Plasmid pTS18 (containing the cDNA sequence in SEQ ID NO. 1) was used in Example 3 as an expression vector.

The resulting pTS18 was deleted by using Exo/Mung DNA Sequencing System (Stratagene), blunted at both terminals, and ligated with self-DNA (FIG. 2). Next, *E. coli* JM109 (Toyobo) was transformed with the deleted plasmid DNA. The nucleotide sequences of the portions of the gene into which deletion mutation was introduced were completely determined using ABI PRISM Cycle Sequencing Kit (Parkin Elmer) both on the sense and anti-sense chains.

The determined partial sequences were used to establish the complete amino acid sequence and cDNA sequence (SEQ ID NO.2) of the antitumor protein. A deduced molecular weight was about 62 kDa. The amino acid sequence on the N terminal (SEQ ID NOS.3 and 4) agreed with the amino acid sequence 2–30 and the amino acid sequence 2–58 in SEQ ID NO.1.

Also, the sequences of the peptide fragments (SEQ ID NOS.5–18) agreed with the amino acid sequence in SEQ ID NO.1 as follows:

SEQ ID NO.5: 59–77 in SEQ ID NO.1;
SEQ ID NO.6: 89–149 in SEQ ID NO.1;
SEQ ID NO.7: 150–178 in SEQ ID NO.1;
SEQ ID NO.8: 179–209 in SEQ ID NO.1;
SEQ ID NO.9: 210–267 in SEQ ID NO.1;
SEQ ID NO.10: 268–297 in SEQ ID NO.1;
SEQ ID NO.11: 298–355 in SEQ ID NO.1;
SEQ ID NO.12: 356–406 in SEQ ID NO.1;
SEQ ID NO.13: 407–436 in SEQ ID NO.1;
SEQ ID NO.14: 437–486 in SEQ ID NO.1;
SEQ ID NO.15: 487–521 in SEQ ID NO.1;
SEQ ID No.16: 522–554 in SEQ ID NO.1;
SEQ ID No.17: 555–566 in SEQ ID NO.1;
SEQ ID No.18: 78–99 in SEQ ID NO.1.

These peptide fragments are useful as antigens for obtaining an antibody against the antitumor protein which can be used in a method for screening and purifying an antitumor protein.

Example 3

Production of Antitumor Protein (1)

Competent cells (JM109 strain; Toyobo) stored at −80° C. were melted, and 100 µl of the cells was transferred to Falcon tube (code 2059). It was mixed with deleated clones of pTS18 (Example 2) and allowed to stand in iced water for 30 min. After exposed to a thermal shock (42° C.) for 30 s, it was cooled in ice for 2 min. After 900 µl SOC culture was added, it was incubated at 37° C. for 1 hour with shaking. The cells were then planted in an LB/Amp plate in an appropriate amount, and incubated overnight at 37° C. A colony having an area of a platinum ring that appeared on the plate was transplanted to a liquid LB culture (containing Amp), and incubated at 37° C. until absorption at 660 nm (Abs660) increased to about 0.2. Then, after IPTG was added to a final concentration of 10 mM, the culture was incubated until Abs660 increased to about 1.

The cells were suspended in the extract (50 mM Tris-HCl, pH 7.5) used in Example 1 (1), which contained PI, and ultrasonically destroyed. After the extract (50 mM Tris-HCl) was centrifuged, the supernatant was recovered in the eluate via affinity chromatography (CNBr-activated Sepharose 6MB resin; Pharmacia) binding the antibody described in Example 1 (2).

The eluate was analyzed by SDS-PAGE combined with Western blotting using the antibody described in Example 1 (2). The result showed that the protein according to the present invention was expressed in the host cell.

Example 4

Production of Antitumor Protein (2)

(1) Preparation of Expression Vector pET-28a

A DNA fragment encoding the antitumor protein was generated by polymerase chain reaction (PCR) using plasmid pTS18 (10 ng)(Example 2) as a template DNA. PCR reaction was carried out using reagents packaged in a commercialy available kit (TAKARA Co.) and the following primers (5 pmole, each) in accordance with a manufacturer's manual.

```
                                          (SEQ ID NO. 19)
Primer 1: GAGAGACCATGGGGTATCGTCTTTCC
                                          (SEQ ID NO. 20)
Primer 2: GAGAGAGGATCCGGAGACGCCAAGGAT
```

After the PCR reaction, the product was digested by NcoI and BamHI. The resulting fragment (0.1 µg) was ligated into the NcoI/BamHI site of pET-28a (0.5 µg) (Novagen).

The resulting DNA construct was introduced into competent cells (*E. Coli*, DH5α and JM109 strains; Toyobo). The plasmid DNA which was harvested from the transformed cells was introduced into competent cells (BL21 (DE3) strain; Novagen).

(2) Preparation of Expression Vector pET-28b

A DNA fragment encoding the antitumor protein was prepared by digesting plasmid pTS18 (Example 2) by EcoRI and XhoI and collecting EcoRI/XhoI fragments. The resulting fragments (0.1 µg) were ligated into the EcoRI/XhoI site of pET-28b (0.5 µg)(Novagen).

The resulting DNA construct was introduced into competent cells (*E. Coli*, DH5α and JM109 strains; Toyobo). The plasmid DNA which was harvested from the transformed cells was introduced into competent cells (BL21 (DE3) strain; Novagen).

(3) Expression of Antitumor Protein Gene

One loopful of the transformed cells, BL21 (DE3) strain having pET-28a and BL21 (DE3) strain having pET-28b, obtained as described in Example 3 (1) and (2) were inoculated on 1 ml of NZYM medium containing 50 µg/ml of Kanamycin and preincubated at 37° C. overnight. 100 µl taken from the cultured medium was inoculated on 10 ml of NZYM medium containing 50 µg/ml of kanamycin and incubated at 25° C. until Abs600 increased to about 0.4. After IPTG was added to a final concentration of 1.0 mM, the culture was incubated for 24 hours.

The cells were harvested from the culture medium, suspended in the extract (25 mM Tris-HCl, pH 7.0) used in Example 1 (1) containing PI, and ultrasonically destroyed.

After the extract (25 mM Tris-HCl, pH 7.0) was centrifuged, the precipitate was recovered. The precipitate was analyzed by SDS-PAGE. A single band was observed on the position of 65 kDa.

The precipitate was also analyzed by Western blotting using the antibody described in Example 1 (2). An immunoreactive band was observed at the same position as that observed on the SDS-PAGE gel. This result showed that the gene of the antitumor protein was expressed in the host cells.

What is claimed is:

1. An isolated nucleotide molecule which encodes a protein comprising the amino acid sequence of SEQ ID NO. 1.

2. A nucleotide molecule according to claim 1, which encodes a protein consisting of the amino acid sequence of SEQ ID NO. 1.

3. A nucleotide molecule according to claim 1, wherein the nucleotide molecule comprises the nucleotide sequence of SEQ ID NO. 2.

4. A nucleotide molecule according to claim 1 comprising the nucleotide sequence of SEQ ID NO. 2.

5. A nucleotide molecule according to claim 1 which is from *Tricholoma matsutake*.

6. A vector comprising a nucleotide molecule according to claim 1.

7. A vector according to claim 6, which is selected from the group consisting of plasmid vectors, virus vectors, and liposome vectors.

8. A vector according to claim 6, which is selected from the group consisting of pBluescript SK(−), pBluescript (+), pRIT2T, pBPV, pSVK3, pET vector, and pQE vector.

9. An isolated host cell comprising the vector according to claim 6.

10. A host cell according to claim 9, which is selected from the group consisting of *E. coli*, a yeast cell, *Bacillus subtilis*, a CHO cell, a COS cell, a human keratinocyte, a C127 cell, a mouse 3T3 cell, a FR3T3 cell, and an HB101 cell.

11. A host cell according to claim 9 which is *E. coli* selected from the group consisting of a SOLR strain, a JM109 strain, a SURE strain, a TOP strain, and a BL21 strain.

12. A host cell according to claim 9 which is a yeast YRG-2 strain.

13. A process for preparing a protein, comprising culturing a host cell comprising a nucleotide molecule according to claim 1 which encodes the protein, and isolating the protein from a culture medium.

\* \* \* \* \*

UNITED STATES PATENT AND TRADEMARK OFFICE
CERTIFICATE OF CORRECTION

PATENT NO. : 6,762,296 B2
DATED : July 13, 2004
INVENTOR(S) : Kawamura et al.

It is certified that error appears in the above-identified patent and that said Letters Patent is hereby corrected as shown below:

Title page,
Item [73], Assignee, change from "Independent Administrative Food Research Institute" to -- 1) Independent Administrative Corporation Food Research Institute (JP) and 2) Momoya Co, Ltd. (JP) --.

Signed and Sealed this

First Day of November, 2005

JON W. DUDAS
*Director of the United States Patent and Trademark Office*